(12) United States Patent
Lautt

(10) Patent No.: US 8,673,964 B2
(45) Date of Patent: Mar. 18, 2014

(54) USE OF DRUG COMBINATIONS FOR TREATING INSULIN RESISTANCE

(75) Inventor: Wilfred Wayne Lautt, Winnipeg (CA)

(73) Assignee: DiaMedica Inc. (CA)

(*) Notice: Subject to any disclaimer, the term of this patent is extended or adjusted under 35 U.S.C. 154(b) by 971 days.

(21) Appl. No.: 11/597,032

(22) PCT Filed: May 20, 2005

(86) PCT No.: PCT/CA2005/000775
§ 371 (c)(1),
(2), (4) Date: May 7, 2008

(87) PCT Pub. No.: WO2005/112949
PCT Pub. Date: Dec. 1, 2005

(65) Prior Publication Data
US 2009/0233995 A1 Sep. 17, 2009

Related U.S. Application Data

(60) Provisional application No. 60/572,486, filed on May 20, 2004.

(51) Int. Cl.
| | | |
|---|---|---|
| *A61K 31/385* | (2006.01) | |
| *A61K 31/27* | (2006.01) | |
| *A61K 31/198* | (2006.01) | |
| *A61K 31/155* | (2006.01) | |
| *A61K 31/4439* | (2006.01) | |
| *A61K 31/7036* | (2006.01) | |
| *A61K 31/4965* | (2006.01) | |
| *A61P 3/10* | (2006.01) | |

(52) U.S. Cl.
USPC ........... 514/440; 514/479; 514/562; 514/635; 514/342; 514/255.06; 514/42

(58) Field of Classification Search
USPC .................. 514/440, 479, 562, 635, 342, 42, 514/255.06
See application file for complete search history.

(56) References Cited

U.S. PATENT DOCUMENTS

| 5,561,165 A * | 10/1996 | Lautt et al. ............. 514/667 |
| 5,762,922 A * | 6/1998 | Noble et al. ............ 424/85.4 |
| 2003/0235609 A1* | 12/2003 | Lautt ...................... 424/450 |

FOREIGN PATENT DOCUMENTS

| CA | 2 415 392 | 1/2002 |
| CA | 2 465 632 | 5/2003 |
| WO | 00/19992 | 4/2000 |

OTHER PUBLICATIONS

Yki-Jarvinen (Cobination Therapies with Insulin in Type 2 diabetes, Deabetes care, vol. 24, No. 4, pp. 758-767).*
Holz (Glucagol-Like Peptide-1 Synthetic Analogs: New Therapeutic Agents for Use in the Treatment of Diabetes Mellitus, Curr Med Chem, Nov. 2003, 10(22): pp. 2471-2483).*
Nodari (Efficacy and tolerability of the long-term administration of carvedilol in patients with chronic heart failure with and without concomitant diabetes mellitus, The European Journal of Heart Failure, 2003, vol. 4, pp. 803-809).*
Beyer et al. "Assessment of Insulin Needs in Insulin-Dependent Diabetics and Healthy Volunteers under Fasting Conditions" Horm Metab Res Suppl 1990; vol. 24 p. 71-77.
Brownlee "Biochemistry and molecular cell biology of diabetic complications" Nature vol. 414, Dec. 2001 p. 813-820.
Hsu et al. "Five Cysteine-Containing Compounds Delay Diabetic Deterioration in Balb/cA Mice" J. Nutr, 2004 134:3245-3249.
Lautt "Hepatic Parasympathetic Neuropathy as cause of Maturity-Onset Diabetes?" Gen. Pharmac. vol. 11 p. 343-345.
Xie et al. "Induction of insulin resistance by cholinergic blockade with atropine in the cat" J. Auton. Pharmacol. (1995) 15, p. 361-369.
Lautt et al. "Hepatic parasympathetic (HISS) control of insulin sensitivity determined by feeding and fasting" American Journal of Physiology—Gastrointestinal and Liver Physiology 281: p. G29-G36 (2001).
Lautt "The HISS story overview: a novel hepatic neurohumoral regulation of peripheral insulin sensitivity in health and diabetes" Canadian Journal of Physiology and Pharmacology 77: p. 553-562 (1999).
Ling et al. "Hyperglycemia Induced by Glucose Infusion Causes Hepatic Oxidative Stress and Systemic Inflammation, But Not STAT3 or MAP Kinase Activation in Liver in Rats" Metabolism vol. 52, No. 7 p. 868-874 (2003).
Moore et al. "Effect of hepatic denervation on peripheral insulin sensitivity in conscious dogs" American Journal of Physiology—Endocrinology and Metabolism 282: p. E286-E296, (2002).
Lautt "New Paradigm for Insulin Resistance: The HISS Story" Atherosclerosis, Hypertension and Diabetes, Kluwer Academic Publishers, Boston 2003. p. 263-276.
Porszasz et al. "The sensory nitrergic nature of the hepatic insulin sensitizing substance mechanism in conscious rabbits" European Journal of Pharmacology 443 (2002) p. 211-212.
Latour et al. "A Rapid Insulin Sensitivity Test (RIST) in the Anesthetized Mice" Diabetes 51 p. A422, 1734-P.
Definition of "cholinergic", www.merriam-webster.com/dictionmy/cholinergic, 1 page (Nov. 10, 2010).
Stedman's Medical Dictionary, 26th Edition (Williams & Wilkins, 1995), pp. 38 and 461-462.

* cited by examiner

*Primary Examiner* — San-Ming Hui
*Assistant Examiner* — Kathrien Cruz

(57) ABSTRACT

The present invention provides pharmaceutical compositions comprising: (a) a modulator of hepatic parasympathetic tone, (b) at least one diabetes drug, and (c) a pharmaceutically acceptable carrier. The present invention includes methods for the treatment and/or prevention of insulin resistance, type 2 diabetes, impaired glucose intolerance, and other associated disorders with pharmaceutical compositions described herein. The invention also provides for a kit comprising a pharmaceutical composition and instructions for its use.

18 Claims, 7 Drawing Sheets aceclidine talsaclidine
(WAL 2014)

USE OF DRUG COMBINATIONS FOR TREATING INSULIN RESISTANCE

This application is a national stage entry under 35 U.S.C. §371 of PCT/CA2005/000775, filed May 20, 2005, which claims benefit of priority under 35 U.S.C. §119(e) of the U.S. Provisional Application No. 60/572,486, filed on May 20, 2004, the entire disclosures of which are hereby incorporated by reference.

FIELD OF INVENTION

The present invention relates to combination drug therapy for the treatment of insulin resistance, and in particular combination therapies which modulate hepatic sympathetic and parasympathetic action.

BACKGROUND

Following a meal, hepatic parasympathetic nerves provide a permissive signal to the liver that regulates the ability of insulin to stimulate the release of a hormone, HISS, from the liver. HISS selectively stimulates glucose uptake and storage as glycogen in skeletal muscle and accounts for over one-half of the whole body glucose disposal that has previously been assumed to be a direct effect of insulin. Hepatic sympathetic nerves block the parasympathetic signal thus preventing the release of HISS and resulting in a 50% reduction in the glucose disposal effect of insulin. This condition is referred to as HISS-dependent insulin resistance (HDIR).

HISS action can be clinically diagnosed by determining the response to insulin in the fasted state and following re-feeding. The difference in the glucose disposal effect of an injection of insulin determined in the fed and fasted state represents the HISS-dependent component of insulin action. The glucose disposal produced in the fasted state is independent of HISS whereas the approximately doubled effect of insulin following a meal is due to both the HISS-dependent and HISS-independent component of insulin action with the difference between the two states being defined as the HISS-dependent component of insulin action.

HISS-dependent and HISS-independent insulin action can be most readily quantitated using the rapid insulin sensitivity test (RIST) which is a transient euglycemic clamp in response to a bolus administration of insulin. Normally insulin injection stimulates removal of glucose from the blood into storage sites with a resultant decrease in blood glucose level occurring. The RIST method uses variable glucose infusion rates to maintain the blood glucose level constant. The amount of glucose required to be administered in order to maintain the glycemic baseline is the index of insulin sensitivity and is referred to as the RIST index. The RIST index produced by this procedure consists of a HISS-dependent component and a HISS-independent component that can be readily differentiated by testing in the control fed state and then repeating the test after blockade of HISS release by any of a number of means including surgical denervation of the liver, blockade of hepatic muscarinic receptors, blockade of hepatic nitric oxide production, or blockade of hepatic cyclooxygenase. Eliminating HISS action by any of these procedures results in a reduction of the RIST index, in the fed state, of approximately 55%. That is, the glucose disposal effect that has been previously attributed to the direct action of insulin on a variety of tissues is actually mediated to a large extent by a hepatic insulin sensitizing process that has previously been unrecognized. This area has recently been reviewed (Lautt, 1999; Lautt, 2003). Blockade of HISS release results in HDIR. If HDIR is produced physiologically in response to fasting, these interventions do not produce any further decrease in insulin action.

HDIR is a normal and essential response to fasting. Insulin release occurs even in the fasted state and performs a number of growth regulating functions. Insulin is released in a pulsatile manner throughout the day with only approximately 50% of insulin release being regulated by food ingestion (Beyer et al., 1990). In the fasting state, it would be disadvantageous for insulin to cause a massive shifting of glucose from blood to skeletal muscle glycogen stores. The glucose disposal action in response to an injection of insulin decreases progressively to insignificance by 24 hours of fasting. This decrease in response to insulin represents a physiologically adjusted decrease in the HISS-dependent component as demonstrated by the observation that the HISS-independent (post-atropine or post-hepatic denervation) component of insulin action is similar in fed and 24-hour fasted rats.

In the immediate postprandial state, approximately 55% of the total glucose disposal effect of a bolus administration of insulin over a wide physiological range (5-100 mu/kg) is accounted for by HISS. By 18 hours of fasting, Sprague Dawley rats show HISS-dependent insulin action that accounts for only 26% of total insulin action (Lautt et al., 2001). The proportion of insulin action accounted for by HISS action remaining after 18 hours of fasting in cats is 35% (Xie & Lautt, 1995) and 25% in dogs (Moore et al., 2002). HISS action in rabbits accounts for approximately 44% of insulin action although the time since feeding was not stated (Porszasz et al., 2002). Fasting induces a 45% reduction in insulin action in mice (Latour & Chan, 2002). Preliminary results indicate that 62% of insulin action in the fed state is accounted for by HISS action in humans. This physiological regulation of HDIR is an appropriate response to fasting and, as such HDIR is a useful physiological state.

While HDIR is a useful physiological state in the fasted condition, failure to release HISS and the resultant HDIR in the fed state is suggested to account for the major metabolic disturbance seen in type 2 diabetes and many other conditions of insulin resistance. According to this model, post-meal nutrient processing normally results in approximately 80% of the glucose absorbed from a meal being stored in the large skeletal muscle mass of the body. Although HISS is released from the liver, it selectively stimulates glucose uptake into glycogen stores in skeletal muscle. Lack of HISS action results in a greatly impaired glucose disposal effect of insulin thus resulting in postprandial hyperglycemia. Additional insulin is released in response to the elevated glucose thus accounting for postprandial hyperinsulinemia in the type 2 diabetic. Insulin stimulates glucose uptake into adipose tissue and into the limited stores of the liver. When the glycogen stores in the liver are saturated, the remaining glucose is converted to lipid thus accounting for postprandial hyperlipidemia in the type 2 diabetic. The biochemical effects of hyperglycemia including the generation of free radicals has been suggested to account for the major non-metabolic pathologies common to diabetics including endothelial cell dysfunction, deposition of atherosclerotic plaques, blindness, renal failure, nerve damage, stroke, and hind limb amputation (Brownlee, 2001). HDIR has been shown to occur in chronic liver disease, fetal alcohol exposed adults, obesity, sucrose fed rats, hypertension, pregnancy and trauma.

The present inventors propose that HDIR is the main cause for type 2 diabetes, impaired glucose tolerance, impaired fasting glucose, hyperinsulinemia, hyperlipidemia, obesity, postprandial hyperglycemia and other insulin resistant states. For patients suffering from these disorders, the only approved form of treatment currently available is insulin and certain oral medications. The oral drugs fall into five main classes: sulfonylureas, biguanides, alpha-glucosidase inhibitors, meglitinide agents and thiazolidinedione agents.

These medications only achieve the best results when combined with a restricted diet and regular exercise. However, even then the treatment is not successful for all patients. Blood glucose levels drop but many never see a decrease to levels that are within the normal range and oral medications are known to spontaneously stop working for unknown reasons. In addition, success rate for individuals who have had type 2 diabetes for more than 10 years is very low. Oral medications are usually successful for the first three years of treatment, but at this point 50% of people with type 2 diabetes need additional therapy. After 9 years, 75% of people need combination treatment to keep their diabetes under control (Turner et al., JAMA 281:2005-2012, 1999)

Combination therapy comprising of two diabetes medications is prescribed in some cases when the single therapy proves to be ineffective. However, the combination of oral therapies is limited, and only certain combinations can be given simultaneously. Sulfonylureas and meglitinide agents can be administered together, but can cause hypoglycemia. Biguanide agents and thiazolidinedione agents cannot be taken with insulin secreting agents and acarbose, a commonly prescribed alpha glucosidase inhibitor cannot be combined with any other anti diabetic agent. The most common result of these combinations is hypoglycemia and weight gain.

Thus, there is a need for more effective and safer combination therapies for the treatment of diabetes and other insulin resistant states. Also, there is a need for treatments that address the specific mechanism involved in post-prandial hyperglycemia, that is, HDIR.

SUMMARY OF THE INVENTION

In a first aspect, the present invention provides a pharmaceutical composition comprising: (a) a modulator of hepatic parasympathetic tone, (b) at least one diabetes drug, and (c) a pharmaceutically acceptable carrier.

In an embodiment of the pharmaceutical composition according to the invention, the modulator of hepatic parasympathetic tone is an NO donor.

In a further embodiment of the pharmaceutical composition according to the invention, the modulator of hepatic parasympathetic tone is a cholinergic agonist and the at least one diabetes drug is a glutathione increasing compound.

In a still further embodiment of the invention, the pharmaceutical composition according to the invention, the modulator of hepatic parasympathetic tone is a bethanechol and the at least one diabetes drug is N-acetylcysteine or α-lipoic acid.

In a second aspect, the present invention provides a pharmaceutical composition comprising: (a) an acetylcholinesterase antagonist, (b) a glutathione increasing compound and (c) a pharmaceutically acceptable carrier.

In a third aspect, the present invention provides a pharmaceutical composition comprising: (a) phosphodiesterase antagonist, (b) a glutathione increasing compound and (c) a pharmaceutically acceptable carrier.

In a fourth aspect, the present invention provides a use of a pharmaceutical composition according to the invention to treat or prevent a disorder selected from a group consisting of: type II diabetes, insulin resistance, impaired glucose intolerance, hyperglycemia, hyperlipideamia, hyperinsulinaemia, impaired glucose metabolism, obesity, diabetic retinopathy, diabetic nephropathy, glomerulosclerosis, syndrome X, hypertension heart disease, cardiovascular disease, stroke, endothelial dysfunction, congestive heart failure, angina, peripheral arterial disease, chronic renal failure, peripheral artery disease and acute renal failure.

In a fifth aspect, the present invention provides a method of treating or preventing a disorder selected from a group consisting of: type II diabetes, insulin resistance, impaired glucose intolerance, hyperglycemia, hyperlipideamia, hyperinsulinaemia, impaired glucose metabolism, obesity, diabetic retinopathy, diabetic nephropathy, glomerulosclerosis, syndrome X, hypertension, heart disease, cardiovascular disease, stroke, endothelial dysfunction, congestive heart failure, angina, peripheral arterial disease, chronic renal failure, acute renal failure and peripheral artery disease, comprising administering a therapeutically effective amount of the pharmaceutical composition according to the invention.

In a sixth aspect, the present invention provides a method of treating or preventing a disorder selected from a group consisting of: type II diabetes, insulin resistance, impaired glucose intolerance, hyperglycemia, hyperlipideamia, hyperinsulinaemia, impaired glucose metabolism, obesity, diabetic retinopathy, diabetic nephropathy, glomerulosclerosis, syndrome X, hypertension, heart disease, cardiovascular disease, stroke, endothelial dysfunction, congestive heart failure, angina, chronic renal failure, acute renal failure and peripheral artery disease, comprising administering a therapeutically effective amount of a modulator of hepatic sympathetic tone and a therapeutically effective amount at least one diabetes drug.

In a seventh aspect, the present invention provides a method of treating or preventing a disorder selected from a group consisting of: type II diabetes, insulin resistance, impaired glucose intolerance, hyperglycemia, hyperlipideamia, hyperinsulinaemia, impaired glucose metabolism, obesity, diabetic retinopathy, diabetic nephropathy, glomerulosclerosis, syndrome X, hypertension, heart disease, cardiovascular disease, stroke, endothelial dysfunction, congestive heart failure, angina, peripheral arterial disease, chronic renal failure, acute renal failure and peripheral artery disease, comprising administering a therapeutically effective amount of an acetylcholinesterase antagonist and a therapeutically effective amount of a glutathione increasing compound.

In an eighth aspect, the present invention provides a method of treating or preventing a disorder selected from a group consisting of: type II diabetes, insulin resistance, impaired glucose intolerance, hyperglycemia, hyperlipideamia, hyperinsulinaemia, impaired glucose metabolism, obesity, diabetic retinopathy, diabetic nephropathy, glomerulosclerosis, syndrome X, hypertension, heart disease, cardiovascular disease, stroke, endothelial dysfunction, congestive heart failure, angina, chronic renal failure, acute renal failure and peripheral artery disease, comprising administering a therapeutically effective amount of an phosphodiesterase antagonist with a glutathione increasing compound.

In a ninth aspect, the present invention provides a kit comprising in combination: the pharmaceutical composition according to any one of claims 1 to 30 and instructions for the dosage regimen for administration of said composition to ameliorate the symptoms a disorder selected from a group consisting of: type II diabetes, insulin resistance, impaired glucose intolerance, hyperglycemia, hyperlipideamia, hyperinsulinaemia, impaired glucose metabolism, obesity, diabetic retinopathy, diabetic nephropathy, glomerulosclerosis, syndrome X, hypertension, heart disease, cardiovascular disease, stroke, endothelial dysfunction, congestive heart failure, angina, chronic renal failure, peripheral artery disease and acute renal failure.

In an embodiment of the invention, the modulator of hepatic parasympathetic tone is a cholinergic agonist selected from a group consisting of: bethanechol, acetylcholine, donepezil, tacrine, edrophonium, demecarium, pyridostigmine, zanapezil, phospholine, metrifonate, neostigmine, phenserine and galathamine.a cholinergic agonist, methacholine, BIBN 99, DIBD, SCH-57790, SCH-217443, SCH-72788, arecoline, an arecoline analogue, xanomeline, alvameline, milameline, RU 47213, sabcomeline, PD-151832, CDD-0034-C, CDD-0102, a spriopiperidine, a spiroqulnuclidine, muscarine, cis-dioxblane, RS86, AF-30, ocvimeline, AF150(S), AF267B, SDZ 210-086, YM-796, a rigid analogue of acetylcholine, acclidine, tasaclidine, oxotremorine, an oxotremorine analogue, pilocarpine, a pilocarpine analogue, thiopilocarpine, and a nitrosylated derivative thereof.

In an embodiment of the invention, the modulator of hepatic parasympathetic tone is an NO donor selected from a group consisting of: an organic nitrate, an organic nitrite, a metal-NO complex, a N-nitrosamine, a N-hydroxy nitrosamine, a nitrosothiol, a C-nitro compound, a diazetine dioxide, a furoxan, a benzofuroxan, a oxatriazole-6-imine, a sydonoimine, an oximine, a hydroxylamine, a N-hydroxyguanidine, a hydroxyurea, a nitrosylated derivative thereof, a pharmaceutical salt thereof, and a mixture thereof.

In an embodiment of the invention, the at least one diabetes drug is selected from a group consisting of: a glutathione increasing compound, an antioxidant, an insulin or an insulin analogue, an α-adrenergic receptor antagonist, a β-adrenergic receptor antagonist, a non-selective adrenergic receptor antagonist, a sulphonylurea, a biguanide agent, a benzoic acid derivative, a α-glucosidase inhibitor, a thiazolidinedione, a phosphodiesterase inhibitor, a cholinesterase antagonist, a GLP-1 analogue and a pharmaceutical salt thereof.

In an embodiment of the invention, the acetylcholinesterase inhibitor is is selected from a group consisting: of phenserine, donepezil, galanthamine, rivastigme, tacrine, physostigmine, neostigmine, edrophonium, pyridostigmine, demecarium, phospholine, metrifonate, zanapezil, ambenonium and combinations thereof.

In an embodiment of the invention, the phosphodiesterase inhibitor is selected from a group consisting of anagrelide, tadalafil, dipyridamole, dyphylline, vardenafil, cilostazol, milrinone, theophylline, sildenafil, caffeine and combinations thereof.

DETAILED DESCRIPTION

While the present invention is not limited to a particular model or mechanism of action, it appears the parasympathetic response to feeding results in the release of acetylcholine which activates muscarinic receptors in the liver. This activation leads to increased production of nitric oxide which stimulates guanyl cyclase activity, resulting in increased levels of cyclic guanosine monophosphate which acts in stimulating the release of HISS. Feeding also results in elevated hepatic glutathione levels. Interruption of any component of this system can result in reduction or abolishment of the parasympathetic response to feeding. Accordingly, insulin resistance and related disorders may be the result of not only abnormal parasympathetic activity but also abnormal sympathetic activity. Thus, the invention provides pharmaceutical compositions and uses thereof for relieving insulin resistance and related disorders and diseases, which correct both hepatic sympathetic and parasympathetic function.

In some instances, the parasympathetic function in response to feeding is impaired due to decreased acetylcholine production or release. In other instances, the parasympathetic function is impaired due to decreased nitric oxide production. The inventors have previously disclosed the use of cholinergic agonists (see for example, U.S. Pat. No. 5,561, 165), the use of nitric oxide donors (see for example, WO 00/19992) for the treatment of insulin resistance and diabetes.

Figure 7:
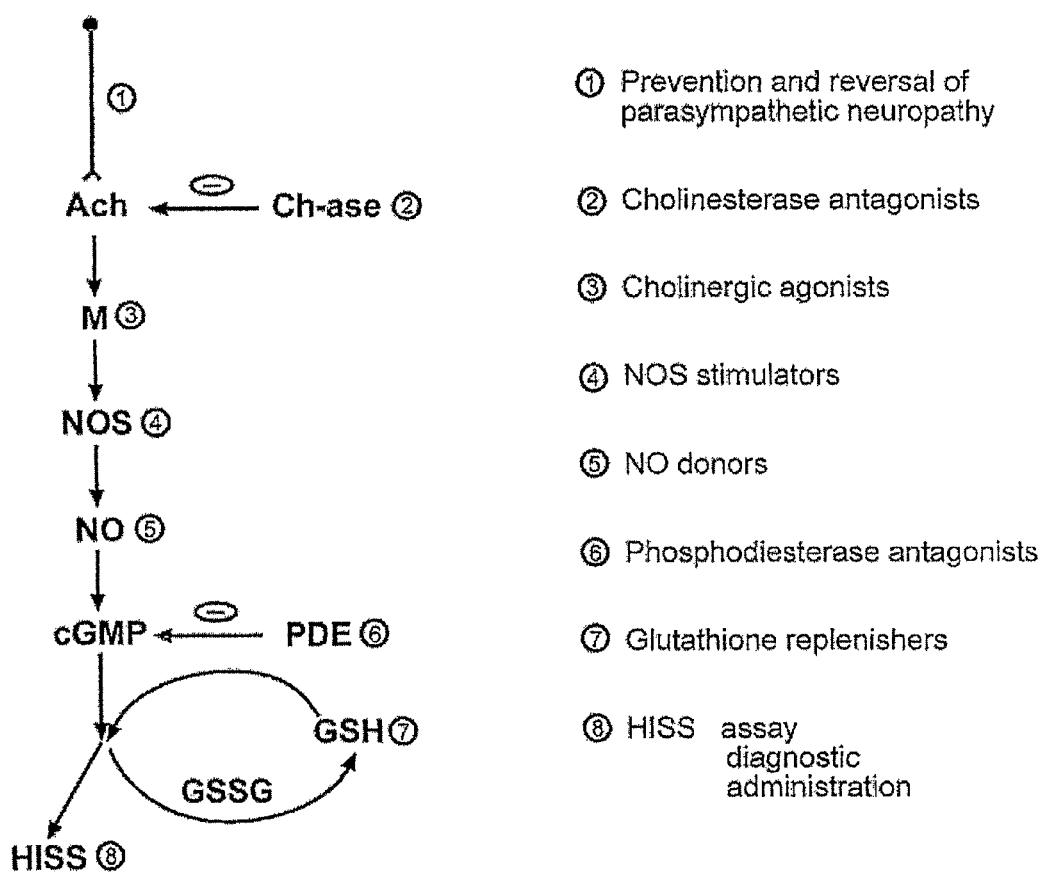
FIG. 7 illustrates the mechanistic pathway of the parasympathetic signalling in the liver.

The inventors have now discovered that the administration of an agent that acts through the hepatic mechanism, as shown in the flow diagram of FIG. 7, is synergistic with existing treatments for insulin resistance, diabetes, and HDIR. Since now we have added. For example, combination therapy comprising the co-administration of a cholinergic agonist with one or more diabetes drugs or the co-administration of a nitric oxide donor with one or more diabetes drugs, or both with a diabetes drug is significantly more effective as compared to conventional combination therapies comprising two or more oral diabetes drug. The inventors have also discovered that combination therapy comprising a cholinergic agonist or a nitric oxide donor and a diabetes drug exhibits significantly less adverse side effects to conventional combination therapies. The inventors have discovered that combination therapy comprising a cholinergic agonist or a nitric oxide donor and a diabetes drug is associated with fewer and less severe incidences of hypoglycemia, edema, weight gain, and liver damage. Furthermore, the inventors discovered that lower dosages of the diabetes drug, as compared to conventional combination therapies, are required to provide glycemic control In particular, the inventors have discovered that the co-administration of a cholinergic agonist and a gluthathione increasing agent results in synergistic improvements in insulin sensitivity. Glutathione (GSH) is a ubiquitous tripeptide that is involved in a variety of vital cellular processes including detoxification and quenching free radicals. There are a number of agents that are available to increase glutathione including glutathione itself (or its esters), α-lipoic acid and the cysteine precursor and rate-limiting agent of GSH biosynthesis, N-acetylcysteine or oxathiazolidine-4-carboxylic acid. The inventors have discovered that treatment with the cholinergic agonist, such as bethanechol, in combination with either N-acetylcysteine or α-lipoic acid or oxathiazolidine-4-carboxylic acid results in synergistic improvements in insulin sensitivity as compared to treatment with either a cholinergic agonist or a glutathione increasing agent alone. In addition, the combination therapy was associated with decreased incidence of gastrointestinal side effects (i.e. nausea, upset stomach, vomiting) which are generally associated with treatment with either bethanechol, N-acetylcysteine or α-lipoic acid alone.

The present inventors have discovered that activation of the parasympathetic pathway through administration of the cholinergic agonist bethanechol, in combination with a glutathione replenishing agent such as N-acetylcysteine, is especially useful for the treatment of several secondary complications of obesity and diabetes, and particularly inflammation (Hsu et al, 2004). Systemic inflammation is highly correlated with morbid obesity and diabetes, and may be responsible for many of the associated pathologies of these diseases. Indeed, even transient episodes of hyperglycemia, such as might occur post-prandially can cause hepatic oxidative stress and release of inflammatory cytokines such as TNF-a and IL-1 (Ling et al, 2004, Hsu et al, 2004). The inventors have determined that bethanechol in combination with N-acetylcysteine is effective in providing relief of these complications, elevating hepatic GSH and improving the HISS response in patients.

The present inventors are the first to identify a vital relationship between parasympathetic response and GSH status in controlling insulin response.

The present invention provides novel pharmaceutical compositions comprising (a) a modulator of hepatic parasympathetic tone, (b) at least one diabetes drug, and (c) a pharmaceutically acceptable carrier. As used herein a "modulator of hepatic parasympathetic tone" is any compound which positively affects the hepatic parasympathetic function. The modulator of hepatic parasympathetic tone may modulate any of the components involved in the hepatic parasympathetic pathway (see FIG. 7). The modulators may be generally be split into two classes: (1) those compounds which modulate cholinergic receptors, for example cholinergic agonists and acetylcholinesterase antagonists, and (2) those compounds which modulate signaling components downstream of cholinergic receptors, for example NOS stimulators, NO donors, and phosphodiesterase antagonists.

In a preferred embodiment of the invention, a novel pharmaceutical composition comprises: (a) a nitric oxide donor, (b) at least diabetes drug, and (c) a pharmaceutical acceptably carrier.

As used herein, any pharmaceutical compound or composition is considered "pharmaceutically acceptable" If: (a) at the dose and method of administration to the patient, it is not acutely toxic, and does not result in chronic toxicity disproportionate to the therapeutic benefit derived from treatment, and (b) the dose and method of administration to the patient reduces insulin resistance in the patient.

As used herein, the phrase, "modulator of hepatic parasympathetic tone" means a compound selected from the group consisting of a cholinergic agonist, an NO donor, an NOS stimulators, bethanechol, acetylcholine, donepezil, tacrine, edrophonium, demecarium, pyridostigmine, zanapezil, phospholine, metrifonate, neostigmine, phenserine and galathamine, a cholinergic agonist, methacholine, BIBN 99, DIBD, SCH-57790, SCH-217443, SCH-72788, arecoline, an arecoline analogue, xanomeline, alvameline, milameline, RU 47213, sabcomeline, PD-151832, CDD-0034-C, CDD-0102, a spriopiperidine, a spiroquinuclidine, muscarine, cis-dioxolane, RS86, AF-30, ocvimeline, AF150(S), AF267B, SDZ 210-086, YM-796, a rigid analogue of acetylcholine, acclidine, tasaclidine, oxotremorine, an oxotremorine analogue, pilocarpine, a pilocarpine analogue, thiopilocarpine, and a nitrosylated derivative thereof, an organic nitrate, an organic nitrite, a metal-NO complex, a N-nitrosamine, a N-hydroxy nitrosamine, a nitrosothiol, a C-nitro compound, a diazetine dioxide, a furoxan, a benzofuroxan, a oxatriazole-6-imine, a sydonoimine, an oximine, a hydroxylamine, a N-hydroxyguanidine, a hydroxyurea, a nitrosylated derivative thereof, a pharmaceutical salt thereof, and a mixture thereof.

Any suitable nitric oxide donor or a pharmaceutical acceptable salt thereof may be used may be used to practice the invention. Examples of suitable nitric oxide donors, include but are not limited to: an organic nitrate, an organic nitrite, a metal-NO complex, a N-nitrosamine, a N-hydroxy nitrosamine, a nitrosothiol, a C-nitro compound, a diazetine dioxide, a furoxan, a benzofuroxan, a oxatriazole-5-imine, a sydonoimine, an oximine, a hydroxylamine, a N-hydroxyguanidine, or a hydroxyurea.

As used herein, the term "diabetes drug" refers to any composition known in the art to be useful in the treatment or prevention of insulin resistance and diabetes. Examples of diabetes drugs which may be used to practice the invention, include but are not limited to:

(a) an antioxidant such as vitamin E, vitamin C, an isoflavone, zinc, selenium, ebselen, a carotenoid;

(b) an insulin or insulin analogue such as regular insulin, lente insulin, semilente insulin, ultralente insulin, NPH or insulin lispro (Humalog®).

(c) an α-adrenergic receptor antagonist such as prazosin, doxazocin, phenoxybenzamine, terazosin, phentolamine, rauwolscine, yohimine, tolazoline, tamsulosin, or terazosin;

(d) a β-adrenergic receptor antagonist such as acebutolol, atenolol, betaxolol, bisoprolol, carteolol, esmolol, metoprolol, nadolol, penbutolol, pindolol, propanolol, timolol, dobutamine hydrochloride, alprenolol, bunolol, bupranolol, carazolol, epanolol, moloprolol, oxprenolol, pamatolol, talinolol, tiprenolol, tolamolol, or toliprolol;

(e) a non-selective adrenergic receptor antagonist such as carvedilol or labetolol;

(f) a first generation sulphonylurea such as tolazamide, tolbutamide, chlorpropamide, or acetohexamide.

(g) a second generation sulphonylurea such as glyburide, glipizide, and glimepiride;

(h) a biguanide agent such as is metformin;

(i) a benzoic acid derivative such as replaglinide;

(j) a α-glucosidase inhibitor such as acarbose and miglitol;

(k) a thiazolidinedione such as rosiglitazone, pioglitazone, or troglitazone;

(l) a phosphodiesterase inhibitor such as anagrelide, tadalfil, dipyridamole, dyphylline, vardenafil, cilostazol, milrinone, theophylline, or caffeine;

(m) a cholineresterase antagonist such as donepezil, tacrine, edrophonium, demecarium, pyridostigmine, zanapezil, phospholine, metrifonate, neostigmine, or galathamine; and (n) a glutathione increasing compound such as N-acetylcysteine, a cysteine ester, L-2-oxothiazolidine-4-carboxolate (OTC), gamma glutamylcysteine and its ethyl ester, glytathtione ethyl ester, glutathione isopropyl ester, lipoic acid, cysteine, methionine, or S-adenosylmethionine.

(o) GLP and glucagon like peptide analogues, such as exanitide, DAC:GLP-1(CJC-1131), Liraglutide, ZP10, BIM51077, LY315902, LY307161 (SR).

In one embodiment of the invention, the pharmaceutical composition comprises 3-morpholinosyndnonimine (SIN-1) as the nitric oxide donor and a sulphonylurea as the diabetes drug. In a preferred embodiment of the invention, the sulphonylurea is glipizide.

In another embodiment of the invention, the pharmaceutical composition comprises 3-morpholinosyndnonimine (SIN-1) as the nitric oxide donor and a α-glucosidase inhibitor as the diabetes drug. In a preferred embodiment of the invention, the α-glucosidase inhibitor is acarbose.

In a further embodiment of the invention, the pharmaceutical composition comprises 3-morpholinosyndnonimine (SIN-1) as the nitric oxide donor and a biguanide agent as the diabetes drug. In a preferred embodiment of the invention, the biguanide inhibitor is metformin.

In a still further embodiment of the invention, the pharmaceutical composition comprises 3-morpholinosyndnonimine (SIN-1) as the nitric oxide donor and a thiazolidinediones as the diabetes drug. In a preferred embodiment of the invention, the thiazolidinedione is pioglitazone.

The pharmaceutical composition comprises 3-morpholinosyndnonimine (SIN-1) as the nitric oxide donor and a biguanide agent as the diabetes drug. In a preferred embodiment of the invention, the biguanide inhibitor is metformin.

In yet a further embodiment of the invention, the pharmaceutical composition comprises 3-morpholinosyndnonimine (SIN-1) as the nitric oxide donor and a benzoic acid derivative as the diabetes drug. In a preferred embodiment of the invention, the benzoic acid derivative is replaglinide.

In yet a further embodiment of the invention, the pharmaceutical composition comprises 3-morpholinosyndnonimine (SIN-1) as the nitric oxide donor and a glutathione replenisher as the diabetes drug. In a preferred embodiment of the invention, the benzoic acid derivative is N-Acetyl Cysteine.

In another embodiment of the invention, the pharmaceutical composition comprises: (a) a cholinergic agonist, (b) at least one diabetes drug, and (c) a pharmaceutically acceptable carrier is provided.

Figure 1:
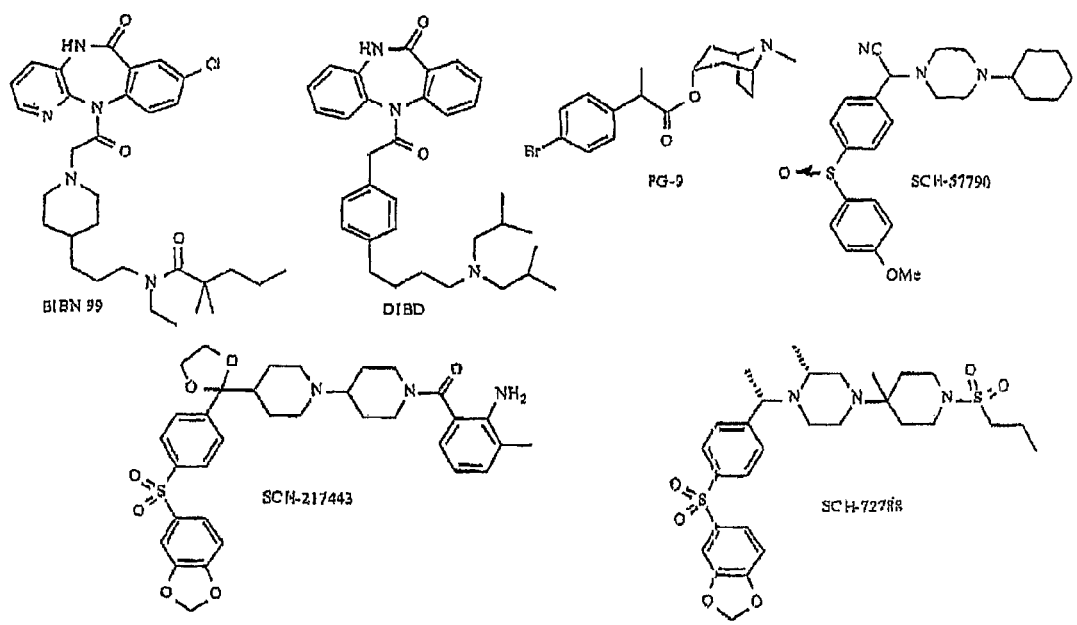
FIG. 1 illustrates the chemical structure for various cholinergic agonists.
Figure 2:
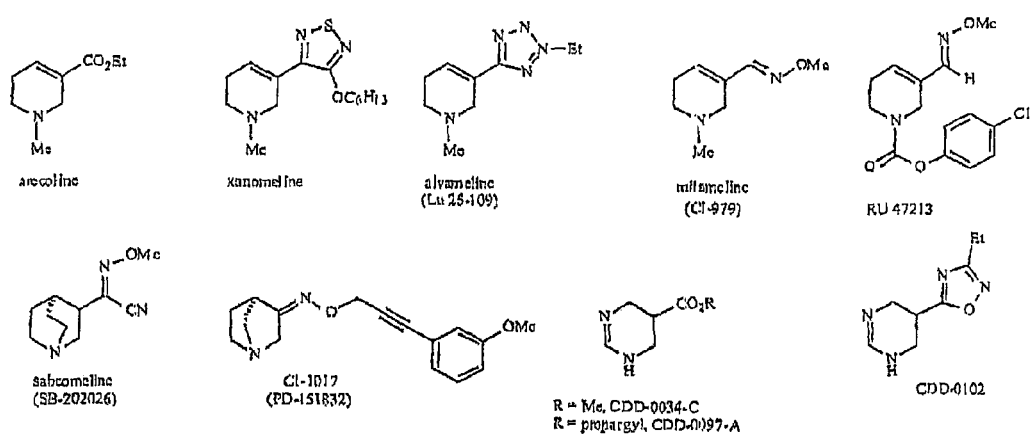
FIG. 2 illustrates the chemical structure for various areoline-analogue cholinergic agonists.
Figure 3:
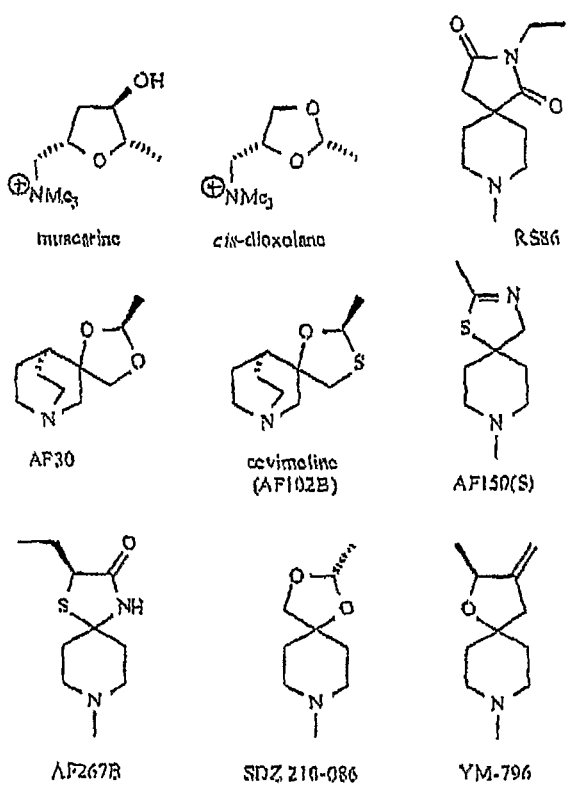
FIG. 3 illustrates the chemical structure for various spriopiperidines and spiroquinuclidines having cholinergic activity.
Figure 4:
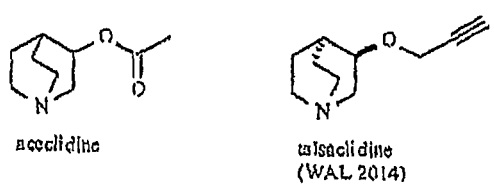
FIG. 4 illustrates the chemical structure for various rigid analogues of acetylcholine having cholinergic activity.
Figure 5:
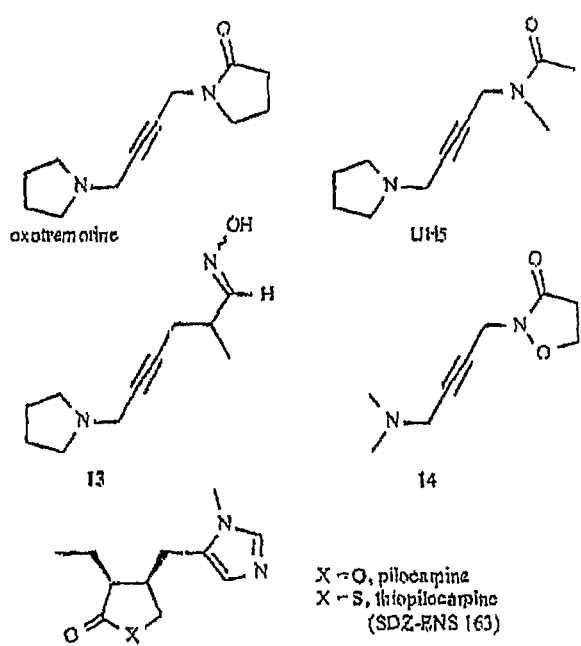
FIG. 5 illustrates the chemical structure for various oxotremorine and pilocarpine cholinergic agonists.

Any suitable cholinergic agonist may be employed to practice the invention. Examples of suitable cholinergic agonists, include, but are not limited to: acetylcholine, methacholine, bethanechol, BIBN 99 (FIG. 1), DIBD (FIG. 1), SCH-57790 (FIG. 1), SCH-217443 (FIG. 1), SCH-72788 (FIG. 1), arecoline (FIG. 2), an arecoline analogue (FIG. 2), xanomeline (FIG. 2), alvameline (FIG. 2), milameline (FIG. 2), RU 47213 (FIG. 2), sabcomeline (FIG. 2), PD-151832 (FIG. 2), CDD-0034-C (FIG. 2), CDD-0102 (FIG. 2), a spiropiperidine (FIG. 3), a spiroquinuclidine (FIG. 3), muscarine (FIG. 3), cis-dioxolane (FIG. 3), RS86 (FIG. 3), AF-30 (FIG. 3), ocvimeline (FIG. 3), AF150(S) (FIG. 3), AF267B (FIG. 3), SDZ 210-086 (FIG. 3), YM-796 (FIG. 3), a rigid analogue of acetylcholine (FIG. 4), acclidine (FIG. 4), tasaclidine (FIG. 4), oxotremorine (FIG. 5), an oxotremorine analogue (FIG. 5), pilocarpine (FIG. 5), a pilocarpine analogue (FIG. 5), or thiopilocarpine (FIG. 5). A nitrosylated form of any these compounds can also be employed.

Preferably, the cholinergic agonist is a muscarnic receptor agonist and more preferably the cholinergic agonist is acetylcholine and most preferably, the cholinergic agonist is bethanechol.

The diabetes drug used with the cholinergic agonist can be any of the diabetes drugs discussed above.

In one embodiment of the invention, pharmaceutical composition comprises bethanechol as the cholinergic agonist and a glutathione increasing compound as the diabetes drug. In preferred embodiment, the pharmaceutical composition comprises bethanechol and N-acetylcystelne as the diabetes drug. In another preferred embodiment, the pharmaceutical composition comprises bethanechol and α-lipoic acid as the diabetes drug.

In another embodiment of the invention, the pharmaceutical composition comprises bethanechol as the cholinergic agonist and a sulphonylurea as the diabetes drug. In a preferred embodiment of the invention, the sulphonylurea is glipizide.

In another embodiment of the invention, the pharmaceutical composition comprises bethanechol as the cholinergic agonist and a α-glucosidase inhibitor as the diabetes drug. In a preferred embodiment of the invention, the α-glucosidase inhibitor is acarbose.

In a further embodiment of the invention, the pharmaceutical composition comprises bethanechol as the cholinergic agonist and a biguanide agent as the diabetes drug. In a preferred embodiment of the invention, the biguanide inhibitor is metformin.

In a still further embodiment of the invention, the pharmaceutical composition comprises bethanechol as the cholinergic agonist and a thiazolidinedlones as the diabetes drug. In a preferred embodiment of the invention, the thiazolidinediones is pioglitazone.

In yet a further embodiment of the invention, the pharmaceutical composition comprises bethanechol as the cholinergic agonist and a benzoic acid derivative as the diabetes drug. In a preferred embodiment of the invention, the benzoic acid derivative is replaglinide.

In another embodiment of the invention, the pharmaceutical composition comprises bethanechol as the cholinergic agonist and a GLP-1 analogue as the diabetes drug. In a preferred embodiment of the invention, the GLP-1 is exanatide.

In another embodiment of the invention, the pharmaceutical composition comprises bethanechol as the cholinergic agonist and an α-adrenergic receptor antagonist as the diabetes drug. In a preferred embodiment of the invention, the α-adrenergic receptor antagonist is prazosin.

In another embodiment of the invention, the pharmaceutical composition comprises bethanechol as the cholinergic agonist and an β-adrenergic receptor antagonist as the diabetes drug. In a preferred embodiment of the invention, the β-adrenergic receptor antagonist is atenolol.

In another embodiment of the invention, the pharmaceutical composition comprises bethanechol as the cholinergic agonist and a non-selective adrenergic receptor antagonist as the diabetes drug. In a preferred embodiment of the invention, the non-selective adrenergic receptor antagonist is carvedilol.

In a still further embodiment of the invention, the pharmaceutical composition comprises a cholinergic agonist, a nitric oxide donor and a diabetes drug such as glipizide, acarbose, metformin, pioglitazone, or repaglinide.

In a second aspect, the invention provides a pharmaceutical composition comprising (a) an acetylcholinesterase antagonist, (b) a glutathione increasing compound and (c) a pharmaceutically acceptable carrier. Examples of acetylcholinesterase inhibitors which may be used to prepare the pharmaceutical composition include, but are not limited to: phenserine, donepezil, galanthamine, rivastigme, tacrine, physostigmine, neostigmine, edrophonium, pyridostigmine, demecarium, phospholine, metrifonate, zanapezil, ambenonium and combinations thereof. The gluthathione increasing compound may be any of the compounds described above. In an preferred embodiment, the gluthathione increasing compound is N-acetylcysteine.

In a third aspect, the invention provides a pharmaceutical composition comprising (a) a phosphodiesterase antagonist, (b) a glutathione increasing compound and (c) a pharmaceutically acceptable carrier. Examples of acetylcholinesterase inhibitors which may be used to prepare the pharmaceutical composition include, but are not limited to: anagrelide, tadalafil, dipyridamole, dyphylline, vardenafil, cilostazol, milrinone, theophylline, sildenafil, caffeine and combinations thereof. The gluthathione increasing compound may be any of the compounds described above. In an preferred embodiment, the gluthathione increasing compound is N-acetylcysteine.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

Administration of compositions of the invention may be made by a variety of suitable routes including oral, topical (including transdermal, buccal or sublingual), nasal, inhalation, and parenteral (including intraperitoneal, subcutaneous, intravenous, intradermal or intramuscular injection) with oral or parenteral being generally preferred. It also will be appreciated that the preferred method of administration and dosage amount may vary with, for example, the condition and age of the recipient.

For injection, the agents of the invention may be formulated in aqueous solutions, preferably in physiologically compatible buffers such as Hanks' solution, Ringer's solution, or physiological saline buffer.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by solid excipient, optionally grinding a resulting mixture, and processing the mixture of granules, after adding suitable auxiliaries, if desired, to obtain tablets or dragee cores. Suitable excipients are, in particular, fillers such as sugars including lactose, sucrose, mannitol, or sorbitol, or cellulose preparations such as; maize starch, wheat starch, rice starch, potato starch, gelatin, gum tragacanth, methyl cellulose, hydroxypropylmethyl-cellulose, sodium carboxymethylcellulose, and/or polyvinylpyrrolidone. If desired, disintegrating agents may be added, such as the cross-linked polyvinylpyrrolidone, agar, or alginic acid or a salt thereof such as sodium alginate.

For administration by inhalation or aerosol, the compositions can be prepared according to techniques well known in the art of pharmaceutical formulation. The compositions can be prepared as solutions in saline, using benzyl alcohol or other suitable preservatives and absorption promoters to enhance bioavailability, fluorocarbons or other solubilizing or dispersing agents known in the art. The compositions of the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Transdermal delivery systems may be passive transdermal delivery systems, or may include the use of skin penetration enhancing agents, or "permeation enhancers," to increase skin permeability, as well as non-chemical modes such as the use of iontophoresis, electroporation or ultrasound.

The pharmaceutical compositions of the present invention may also include various other components which provide additional therapeutic benefit, act to affect the therapeutic action of the pharmaceutical composition, or act towards preventing any potential side effects which may be posed as a result of administration of the pharmaceutical composition. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids, vitamins, and minerals.

The pharmaceutical compositions according to the invention can be used to treat or prevent insulin resistance and diabetes. The pharmaceutical compositions can also be used to treat or prevent other disorders related to insulin resistance such as impaired glucose intolerance, hyperglycemia, hyperlipideamia, hyperinsulinaemia, impaired glucose metabolism, obesity, diabetic retinopathy, diabetic nephropathy, glomerulosclerosis, syndrome X, hypertension, heart disease, cardiovascular disease, stroke, endothelial dysfunction, congestive heart failure, angina, chronic renal failure, acute renal failure and peripheral artery disease.

The precise dose for any of the pharmaceutical compositions of the present invention will depend on a number of factors which will be apparent to those skilled in the art and in light of the disclosure herein. In particular these factors include: the identity of the compounds to be administered, the formulation, the route of administration employed, the patient's gender, age, and weight, and the severity of the condition being treated. Methods for determining dosage and toxicity are well known in the art with studies generally beginning in animals and then in humans if no significant animal toxicity is observed. The appropriateness of the dosage can be assessed by monitoring insulin resistance using the RIST protocol as set out in Lautt et al, 1998. Where the dose provided does not cause insulin resistance to decline to normal or tolerable levels, following at least three days of treatment, the dose can be increased. The patient should be monitored for signs of adverse drug reactions and toxicity, especially with regard to liver and cardiovascular function.

For pharmaceutical compositions comprising a nitric oxide donor, the daily dosage of the nitric oxide donor will between 0.01 mg/kg and 100 mg/kg depending on the particular nitric oxide donor used. Where the nitric oxide donor is SIN-1, the daily dose will between 0.01 mg/kg and 40 mg/kg and preferably 0.15 mg/kg. The daily dosage of the diabetes drug will depend on the particular drug used. Where the drug is glizpide, the daily dosage will between 0.1 mg/kg and 10 mg/kg, and more preferably between 1 mg/kg and 5 mg/kg. Where the diabetes drug is acarbose, the daily dosage will be between 1 and 100 mg/kg, and preferably 10 mg/kg and 40 mg/kg. Where the diabetes drug is metformin, the daily dosage will be between 10 and 1000 mg/kg, and preferably 50 and 200 mg/kg. Where the diabetes drug is pioglitazone, the daily dosage will be between 0.1 and 10 mg/kg, and preferably between 0.5 mg/kg and 5 mg/kg. Where the diabetes drug is repaglinide, the daily dosage will be between 0.1 and 10 mg/kg, and preferably between 0.5 mg/kg and 5 mg/kg.

For pharmaceutical compositions comprising a cholinergic agonist, the daily dosage of the cholinergic agonist will depend on the particular cholinergic agonist used. Where the cholinergic agonist is bethanechol, a single dosage will be between 0.01 mg and 100 mg and preferably between 0.1 mg and 10 mg. Where the cholinergic agonist is bethanechol, a single dosage will be between 0.01 mg and 10 mg and preferably between 0.1 and 10 mg. The amount of the diabetes drug will be the similar to the amounts discussed above. Where the diabetes drug is N-acetylcysteine, a single dosage will be between 100 mg and 5 g, and preferably between 500 mg and 1 g The pharmaceutical composition may be administered to have it peak when blood glucose is high, such as after a meal, so as to allow glucose uptake at that time. The combination of drugs may be formulated into the same pill containing the cholinergic agonist and/or the nitric oxide donor and the diabetes drug. Alternatively, a kit may be used comprising of multiple pills with the appropriate dose of diabetic drug and/or the cholinergic agonist and nitric oxide donor, such as, but not limited to, a "blister pack", including instructions or directions printed on or associated with the packaging.

The pharmaceutical compositions of the present invention can be targeted to the liver of the patient thereby eliminating deleterious systemic effects. The pharmaceutical compositions can be conjugated to bile salts or albumin for preferential delivery to the liver. Alternatively, the pharmaceutical compositions can be encapsulated within liposomes which are preferentially targeted to the liver. The pharmaceutical compositions of the present invention can be administered either in active form or as precursor which is metabolized by to the active form by enzymes in the liver. Where the pharmaceutical composition is targeted to the liver, the dosage may be reduced.

Although the present invention has been described with reference to illustrative embodiments, it is to be understood that the invention is not limited to these precise embodiments, and that various changes and modifications may be effected therein by one skilled in the art. All such changes and modifications are intention to be encompassed in the appended claims.

EXAMPLES

Example 1

Effect of Bethanechol and N-Acetylcysteine on Insulin Sensitivity in Rats with Insulin Resistance Produced by High Sucrose Feeding Animal Groups—Male Sprague Dawley rats having a starting weight of ≥220.0 g (Charles River, St. Constant, Quebec, Canada) were fed a normal rat chow diet and regular tap water, with and without the exposure to a 35% liquid sucrose solution for a 2 week period. Six groups of animals were established under the following treatments: (1) control diet, saline treatment (n=6); (2) control diet, bethanechol (0.5 µg/kg ipv) and N-acetyl-L-cysteine (200 mg/kg) treatment (n=8); (3) control diet, bethanechol (0.5 µg/kg ipv) (n=5); (4) control diet, N-acetyl-L-cysteine (200 mg/kg) (n=4); (5) sucrose diet, saline treatment (n=4); (6) sucrose diet, bethanechol (0.5 µg/kg ipv) and N-acetyl-L-cysteine (200 mg/kg) treatment (n=5); (7) sucrose diet, bethanechol (0.5 µg/kg ipv) (n=6); and (8) sucrose diet, N-acetyl-L-cysteine (200 mg/kg) (n=3).

Methodology—All animals are 24 hour fasted. The animals are prepared using the standard RIST surgical preparation. The rats are anaesthetized with an intraperitoneal injection of sodium pentobarbital (65 mg kg-1; Somnotol, MTC Pharmaceuticals, Ont). Maintained anesthesia is achieved throughout the experiment by a continuous infusion of pentobarbital sodium (0.5 mg·ml-1 saline given at 50 µl·min-1) through a cannula in the jugular vein, supplemented with a 0.65 mg (0.01 ml) bolus injection when required. The rats are placed on a temperature-controlled surgical table (Harvard Apparatus, Kent, England) and rectal temperature is monitored and held at 37-37.5° C. Spontaneous respiration is allowed through a tracheal tube.

An arterial-venous shunt is established, as previous described (Lautt W W et al. *Can J Physiol Pharmacol.* 1998; 76 (12): 1080-6), for monitoring mean arterial blood pressure (MAP), blood glucose level and for drug delivery. Briefly, two catheters (polyethylene tubing PE60), one inserted into the right femoral artery and the other into the right femoral vein, are connected to the two openings of a three way vascular circuit consisting of a T tube connected with silicon tubing. The third opening of the circuit is connected to a pressure transducer for the recording of the shunt pressure which, when the silicon tubing toward the venous side of the circuit is closed by clamping, represented the systemic arterial blood pressure. Blood samples are taken from the arterial side of the shunt for the glucose measurement. Flowing blood within the shunt assures the real time measurement of the blood glucose concentration, which is essential for the euglycemic clamp test as mentioned below. An infusion line is inserted into the venous side of the loop for drug delivery. Another infusion line connected to the jugular vein is established for glucose infusion. Animals are heparinized (100 IU·kg-1) to prevent clotting in the vascular loop.

In addition to the standard RIST surgical preparation, a laparotomy with portal venous puncture (21 g×¾ inch) and an IG puncture (22 gauge, 1 inch iv catheter inserted into the stomach and glued into place) are performed.

A control RIST is performed as previously described (Lautt W W et al. *Can J Physiol Pharmacol.* 1998; 76 (12): 1080-6). Briefly, following completion of surgery, animals are allowed a 30-min stabilization period. The baseline glucose levels are then determined by samples taken at 5-min intervals and continued until three successive stable determinations were made. The mean of these three data points is regarded as the baseline for the RIST. To perform the RIST, human insulin (50 mU·kg-1 in 0.5 ml saline) is infused into the femoral vein at the rate of 0.1 ml·min-1 for 5-min. After 1-min of insulin infusion, the first test glucose sample is determined and a variable glucose infusion (10%) is initiated. Blood samples are taken every 2-min and the glucose infusion rate is adjusted accordingly to maintain euglycemia. The RIST index is the amount of glucose (mg·kg-1) infused, to maintain euglycemia, over the test period that terminated when no further glucose infusion was required (approximately 30 min). At the end of a RIST, the animal is at its pretest glycemic level.

Depending on the test group, the bethanechol or an equivalent volume of saline is administered ipv (0.5 ml bolus, rate of 0.05 ml/min plus 0.03 ml for catheter dead-space volume). Depending on the test group, the N-acetylcysteine or an equivalent volume of saline is then administered iv (1.0 ml bolus, rate of 0.1 ml/min). The animals were allowed to rest for 60 minutes from the initiation of the drug administration. The animals were administered a mixed liquid meal (10 ml/kg) by intragastric infusion (1.0 ml/min, add 0.1 ml test meal to account for catheter dead-space volume). Blood glucose samples were taken every 5 minutes for a minimum of 90 minutes to profile the glycemic response to the test meal. Once a stable glycemia has been achieved, a second RIST is performed. A liver sample is taken for glutathione determination.

Figure 6:
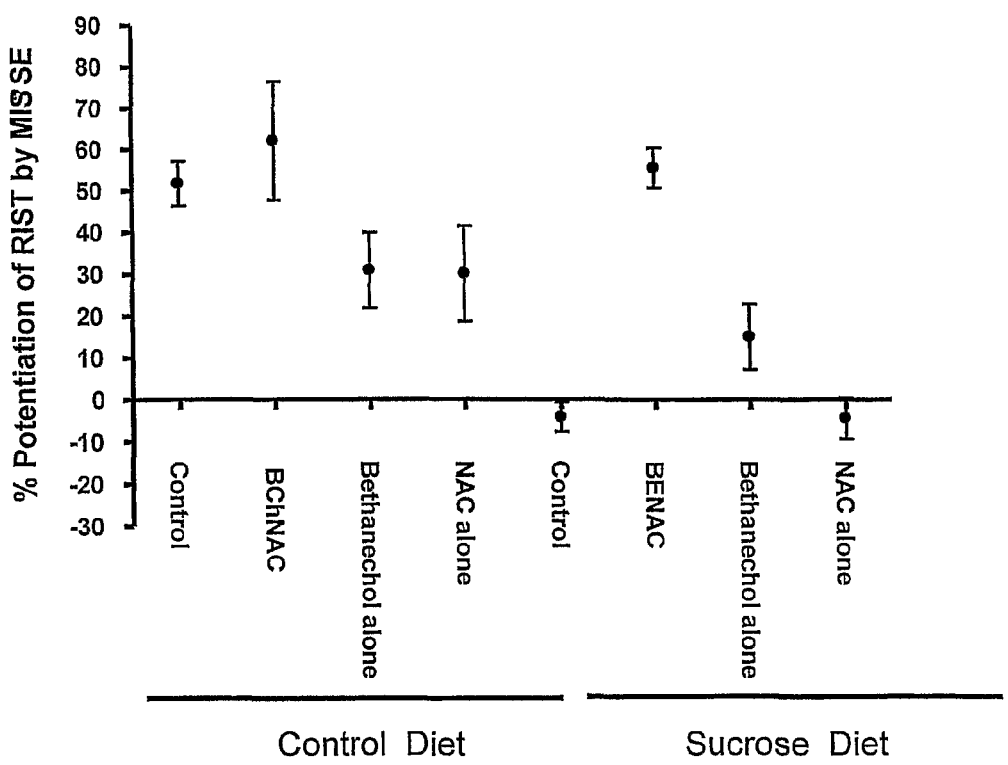
FIG. 6 is a graph comparing the effect of bethanechol and N-acetylcysteine combination therapy on meal induced insulin sensitization in control diet and sucrose diet rats.

Results—As shown in Table 1 and in FIG. 6, rats treated with bethanechol and N-acetylcystelne showed the greatest potentiation in RIST as compared to the control rats. The combination therapy was more effective than either bethanechol or N-acetylcystelne alone for restoring insulin sensitivity in sucrose fed rats.

TABLE 1

Effect of Bethanechol (Bch) and N-acetylcysteine (NAC) combination therapy on meal induced insulin sensitization in sucrose fed rats. All values refer to the percent potentation of RIST as compared to control.

| Control Diet | | | | Sucrose Diet | | | |
|---|---|---|---|---|---|---|---|
| Control | Bch/NAC | BCH alone | NAC alone | Control | Bch/NAC | BCH alone | NAC alone |
| 52.17 | 28.221 | 9.06 | 33.5 | 1.84 | 62.99 | 45.59 | 3 |
| 30.48 | 30.13 | 15.19 | 27.39 | −10 | 45.9 | 13.22 | −13.85 |
| 63.48 | 36.18 | 35.62 | 57.25 | 1.89 | 69.76 | −13.22 | −2.63 |
| 66.99 | 45.13 | 33.87 | 1.89 | −10.68 | 45.25 | 14.22 | |
| 51.291 | 51.07 | 60.33 | | | 53.66 | 7.71 | |
| 45.6 | 109.05 | | | | | 22.36 | |
| | 140.19 | | | | | | |
| | 56.98 | | | | | | |

Example 2

Effect of Bethanechol and Glipizide on Insulin Sensitivity in Rats with Insulin Resistance Produced by High Sucrose Feeding The experiment is completed as described in Example 1 with the N-acetylcysteine being replaced with glipizide. The combination therapy is more effective than either bethanechol or glipizide alone for restoring insulin sensitivity in sucrose fed rats.

Example 3

Effect of Bethanechtol and Acarbose on Insulin Sensitivity in Rats with Insulin Resistance Produced by High Sucrose Feeding The experiment is completed as described in Example 1 with the N-acetylcystelne being replaced with acarbose. The combination therapy is more effective than either bethanechol or acarbose alone for restoring insulin sensitivity in sucrose fed rats.

Example 4

Effect of Bethanechol and Metformin on Insulin Sensitivity in Rats with Insulin Resistance Produced by High Sucrose Feeding The experiment is completed as described in Example 1 with N-acetylcysteine being replaced with metformin. The combination therapy is more effective than either bethanechol or metformin alone for restoring insulin sensitivity in sucrose fed rats.

Example 5

Effect of Bethanechol and Pioglitazone on Insulin Sensitivity in Rats with Insulin Resistance Produced by High Sucrose Feeding The experiment is completed as described in Example 1 with N-acetylcysteine being replaced with pioglitazone. The combination therapy is more effective than either bethanechol or pioglitazone alone for restoring insulin sensitivity in sucrose fed rats.

Example 6

Effect of Bethanechol and Repaglinide on Insulin Sensitivity in Rats with Insulin Resistance Produced by High Sucrose Feeding The experiment is completed as described in Example 1 with N-acetylcysteine being replaced with repaglinide. The combination therapy is more effective than either bethanechol or repaglinide alone for restoring insulin sensitivity in sucrose fed rats.

Example 7

Effect of Neostigmine and N-Acetylcysteine on Insulin Sensitivity in Rats with Insulin Resistance Produced by High Sucrose Feeding The experiment is completed as described in Example 1 with benthanecol being replaced with neostigmine. The combination therapy is more effective than either neostigmine or N-acetylcysteine alone for restoring insulin sensitivity in sucrose fed rats.

Example 8

Effect of SIN-1 and Glipizide on Insulin Sensitivity in Rats with Insulin Resistance Produced by High Sucrose Feeding The experiment is completed as described in Example 1 with bethanechol being replaced with SIN-1 and N-acetylcysteine being replaced with glipizide. The combination therapy is more effective than either SIN-1 or glipizide alone for restoring insulin sensitivity in sucrose fed rats.

Example 9

Effect of SIN-1 and Acarbose on Insulin Sensitivity in Rats with Insulin Resistance Produced by High Sucrose Feeding The experiment is completed as described in Example 1 with bethanechol being replaced with SIN-1 and N-acetylcysteine being replaced with acarbose. The combination therapy is more effective than either SIN-1 or acarbose alone for restoring insulin sensitivity in sucrose fed rats.

Example 10

Effect of SIN-1 and Metformin on Insulin Sensitivity in Rats with Insulin Resistance Produced by High Sucrose Feeding The experiment is completed as described in Example 1 with bethanechol being replaced with SIN-1 and N-acetylcysteine being replaced with metformin. The combination therapy was more effective than either SIN-1 or metformin alone for restoring insulin sensitivity in sucrose fed rats.

Example 11

Effect of SIN-1 and Pioglitazone on Insulin Sensitivity in Rats with Insulin Resistance Produced by High Sucrose Feeding The experiment is completed as described in Example 1 with bethanechol being replaced with SIN-1 and N-acetylcysteine being replaced with pioglitazone. The combination therapy is more effective than either SIN-1 or pioglitazone alone for restoring insulin sensitivity in sucrose fed rats.

Example 12

Effect of SIN-1 and Repaglinide on Insulin Sensitivity in Rats with Insulin Resistance Produced by High Sucrose Feeding The experiment is completed as described in Example 1 with bethanechol being replaced with SIN-1 and N-acetylcysteine being replaced with repaglinide. The combination therapy is more effective than either SIN-1 or repaglinide alone for restoring insulin sensitivity in sucrose fed rats.

Example 13

Effect of Zaprinast and N-Acetylcysteine on Insulin Sensitivity in Rats with Insulin Resistance Produced by High Sucrose Feeding The experiment is completed as described in Example 1 with bethanechol being replaced with zaprinast. The combination therapy is more effective than either zaprinast or n-acetylcysteine alone for restoring insulin resistance in sucrose fed rats,

Example 14

Effect of SIN-1 and Bethanechol on Insulin Sensitivity in Rats with Insulin Resistance Produced by Hepatic Denervation An animal is prepared as in Example 1. A control RIST is done. The response is within normal range. A RIST is then done after surgical denervation of the hepatic nerves reaching the liver along the hepatic artery and the index shows insulin resistance. Bethanechol is administered by infusion into the portal vein at a rate of 2.5 mg/kg/min beginning 10 minutes prior to the insulin administration and continuing for the entire test period. The resulting RIST index shows reversal of the insulin resistance.

On a second animal, a control RIST is done. The response is within the normal range. A RIST is then done after surgical denervation and the RIST index shows significant insulin resistance. SIN-1 is administered by infusion into the portal vein at a rate of 10.0 mg/kg/min for a period of 2 minutes. The resulting RIST index shows reversal of the insulin resistance.

On a third animal a control RIST is done. The response is within the normal range. A RIST is then done after surgical denervation and the RIST index shows significant insulin resistance. First bethanechol is administered as described above. Five minutes prior to the end of the test period SIN-1 is administered by infusion into the portal vein at a rate of 10.0 mg/kg/min for a period of 2 minutes. The resulting RIST index shows a greater reversal of insulin resistance than when each of bethanechol and SIN-1 was given alone.

Example 15

Effect of SIN-1, Bethanechol and 5 Mg/Kg of Glipizide on Insulin Sensitivity in Rats with Insulin Resistance Produced by Hepatic Denervation An animal is prepared as in Example 1. A control RIST is done. The response is within normal range. A RIST is then done after surgical denervation. Bethanechol is administered by infusion into the portal vein at a rate of 2.5 mg/kg/min beginning 10 minutes prior to the insulin administration and continuing for the entire test period. The resulting RIST index shows reversal of the insulin resistance.

On a second animal, a control RIST is done. The response is within the normal range. A RIST is then done after surgical denervation and the RIST index shows significant insulin resistance. SIN-1 is administered by infusion into the portal vein at a rate of 10.0 mg/kg/min for a period of 2 minutes. The resulting RIST index shows reversal of the insulin resistance.

On a third animal a control RIST is done. The response is within the normal range. A RIST is then done after surgical denervation and the RIST index shows significant insulin resistance. First bethanechol is administered as described above. Five minutes prior to the end of the test period SIN-1 is administered by infusion into the portal vein at a rate of 10.0 mg/kg/min for a period of 2 minutes. Thirty seconds prior to the end of the test period a bolus injection of 5 mg/kg of glipizide is given. A RIST is taken and the result is greater insulin resistance than bethanechol or SIN-1 alone.

Example 16

Effect of SIN-1, Bethanechol and 2.5 Mg/Kg of Glipizide on Insulin Sensitivity in Rats with Insulin Resistance Produced by Hepatic Denervation An animal is prepared as in Example 1. A control RIST is done. The response is within normal range. A RIST is then done after surgical denervation. Bethanechol is administered by infusion into the portal vein at a rate of 2.5 mg/kg/min beginning 10 minutes prior to the insulin administration and continuing for the entire test period. The resulting RIST index shows reversal of the insulin resistance.

On a second animal, a control RIST is done. The response is within the normal range. A RIST is then done after surgical denervation and the RIST index shows significant insulin resistance. SIN-1 is administered by infusion into the portal vein at a rate of 10.0 mg/kg/min for a period of 2 minutes. The resulting RIST index shows reversal of the insulin resistance.

On a third animal a control RIST is done. The response is within the normal range. A RIST is then done after surgical denervation and the RIST index shows significant insulin resistance. First bethanechol is administered as described above. Five minutes prior to the end of the test period SIN-1 is administered by infusion into the portal vein at a rate of 10.0 mg/kg/min for a period of 2 minutes. Thirty seconds prior to the end of the test period a bolus injection of 2.5 mg/kg of glipizide is given. A RIST is taken and the result is greater insulin resistance than bethanechol or SIN-1 alone.

Example 17

Effect of SIN-1, Bethanechol and 2.5 Mg/Kg of Glipizide on Insulin Sensitivity in Rats with Insulin Resistance Produced by Hepatic Denervation An animal is prepared as in Example 1. A control RIST is done. The response is within normal range. A RIST is then done after surgical denervation. Bethanechol is administered by infusion into the portal vein at a rate of 2.5 mg/kg/min beginning 10 minutes prior to the insulin administration and continuing for the entire test period. The resulting RIST index shows reversal of the insulin resistance.

On a second animal, a control RIST is done. The response is within the normal range. A RIST is then done after surgical denervation and the RIST index shows significant insulin resistance. SIN-1 is administered by infusion into the portal vein at a rate of 10.0 mg/kg/min for a period of 2 minutes. The resulting RIST index shows reversal of the insulin resistance.

On a third animal a control RIST is done. The response is within the normal range. A RIST is then done after surgical denervation and the RIST index shows significant insulin resistance. First bethanechol is administered as described above. Five minutes prior to the end of the test period SIN-1 is administered by infusion into the portal vein at a rate of 10.0 mg/kg/min for a period of 2 minutes. Thirty seconds prior to the end of the test period a bolus injection of 1.25 mg/kg of glipizide is given. A RIST is taken and the result is greater insulin resistance than bethanechol or SIN-1 alone.

Example 18

Effect of SIN-1, Bethanechol and Acarbose on Insulin Sensitivity in Rats with Insulin Resistance Produced by Hepatic Denervation An animal is prepared as in Example 1. A control RIST is done. The response is within normal range. A RIST is then done after surgical denervation. Bethanechol is administered by infusion into the portal vein at a rate of 2.5 mg/kg/min beginning 10 minutes prior to the insulin administration and continuing for the entire test period. The resulting RIST index shows reversal of the insulin resistance.

On a second animal, a control RIST is done. The response, is within the normal range. A RIST is then done after surgical denervation and the RIST index shows significant insulin resistance. SIN-1 is administered by infusion into the portal vein at a rate of 10.0 mg/kg/min for a period of 2 minutes. The resulting RIST index shows reversal of the insulin resistance.

On a third animal a control RIST is done. The response is within the normal range. A RIST is then done after surgical denervation and the RIST index shows significant insulin resistance. First bethanechol is administered as described above. Five minutes prior to the end of the test period SIN-1 is administered by infusion into the portal vein at a rate of 10.0 mg/kg/min for a period of 2 minutes. Thirty seconds prior to the end of the test period a bolus injection of 40 mg/kg, 20 mg/kg or 10 mg/kg of acarbose is given. A RIST is taken and the result is greater insulin resistance than bethanechol or SIN-1 alone. The lower doses of acarbose are as effective as the higher doses.

Example 19

Effect of SIN-1, Bethanechol and Metformin on Insulin Sensitivity in Rats with Insulin Resistance Produced by Hepatic Denervation An animal is prepared as in Example 1. A control RIST is done. The response is within normal range. A RIST is then done after surgical denervation. Bethanechol is administered by infusion into the portal vein at a rate of 2.5 mg/kg/min beginning 10 minutes prior to the insulin administration and continuing for the entire test period. The resulting RIST index shows reversal of the insulin resistance.

On a second animal, a control RIST is done. The response is within the normal range. A RIST is then done after surgical denervation and the RIST index shows significant insulin resistance. SIN-1 is administered by infusion into the portal vein at a rate of 10.0 mg/kg/min for a period of 2 minutes. The resulting RIST index shows reversal of the insulin resistance.

On a third animal a control RIST is done. The response is within the normal range. A RIST is then done after surgical denervation and the RIST index shows significant insulin resistance. First bethanechol is administered as described above. Five minutes prior to the end of the test period SIN-1 is administered by infusion into the portal vein at a rate of 10.0 mg/kg/min for a period of 2 minutes. Thirty seconds prior to the end of the test period a bolus injection of 200 mg/kg, 100 mg/kg or 50 mg/kg of metformin is given. A RIST is taken and the result is greater insulin resistance than bethanechol or SIN-1 alone. The lower doses of metformin are as effective as the higher doses.

Example 20

Effect of SIN-1, Bethanechol and Pioglitazone on Insulin Sensitivity in Rats with Insulin Resistance Produced by Hepatic Denervation An animal is prepared as in Example 1. A control RIST is done. The response is within normal range. A RIST is then done after surgical denervation. Bethanechol is administered by infusion into the portal vein at a rate of 2.5 mg/kg/min beginning 10 minutes prior to the insulin administration and continuing for the entire test period. The resulting RIST index shows reversal of the insulin resistance.

On a second animal, a control RIST is done. The response is within the normal range. A RIST is then done after surgical denervation and the RIST index shows significant insulin resistance. SIN-1 is administered by infusion into the portal vein at a rate of 10.0 mg/kg/min for a period of 2 minutes. The resulting RIST index shows reversal of the insulin resistance.

On a third animal a control RIST is done. The response is within the normal range. A RIST is then done after surgical denervation and the RIST index shows significant insulin resistance. First bethanechol is administered as described above. Five minutes prior to the end of the test period SIN-1 is administered by infusion into the portal vein at a rate of 10.0 mg/kg/min for a period of 2 minutes. Thirty seconds prior to the end of the test period a bolus injection of 3 mg/kg, 1.5 mg/kg and 0.75 mg/kg of pioglitazone is given. A RIST is taken and the result is greater insulin resistance than bethanechol or SIN-1 alone. The lower doses of pioglitazone are as effective as the higher doses.

Example 21

Effect of SIN-1, Bethanechol and Repaglinide on Insulin Sensitivity in Rats with Insulin Resistance Produced by Hepatic Denervation An animal is prepared as in Example 1. A control RIST is done. The response is within normal range. A RIST is then done after surgical denervation. Bethanechol is administered by infusion into the portal vein at a rate of 2.5 mg/kg/min beginning 10 minutes prior to the insulin administration and continuing for the entire test period. The resulting RIST index shows reversal of the insulin resistance.

On a second animal, a control RIST is done. The response is within the normal range. A RIST is then done after surgical denervation and the RIST index shows significant insulin resistance. SIN-1 is administered by infusion into the portal vein at a rate of 10.0 mg/kg/min for a period of 2 minutes. The resulting RIST index shows reversal of the insulin resistance.

On a third animal a control RIST is done. The response is within the normal range. A RIST is then done after surgical denervation and the RIST index shows significant insulin resistance. First bethanechol is administered as described above. Five minutes prior to the end of the test period SIN-1 is administered by infusion into the portal vein at a rate of 10.0 mg/kg/min for a period of 2 minutes. Thirty seconds prior to the end of the test period a bolus injection of 3 mg/kg, 1.5 mg/kg and 0.75 mg/kg of repaglinide is given. A RIST is taken and the result is greater insulin resistance than bethanechol or SIN-1 alone. The lower doses of repaglinide are as effective as the higher doses.

Example 22

Effect of Bethanechol, NAC and Repaglinide on Insulin Sensitivity in Rats with Insulin Resistance Produced by Hepatic Denervation An animal is prepared as in Example 1. A control RIST is done. The response is within normal range. A RIST is then done after surgical denervation. Bethanechol is administered by infusion into the portal vein at a rate of 2.5 mg/kg/min beginning 10 minutes prior to the insulin administration and continuing for the entire test period. The resulting RIST index shows reversal of the insulin resistance.

On a second animal, a control RIST is done. The response is within the normal range. A RIST is then done after surgical denervation and the RIST index shows significant insulin resistance. NAC (200 mg/mL) is administered by infusion into the portal vein at a rate of 0.1 mL/min for a period of 2 minutes. The resulting RIST index shows reversal of the insulin resistance.

On a third animal a control RIST is done. The response is within the normal range. A RIST is then done after surgical denervation and the RIST index shows significant insulin resistance. First bethanechol is administered as described above. Five minutes prior to the end of the test period NAC is administered by infusion into the portal vein at a rate of 0.1 mL/min for a period of 2 minutes. Thirty seconds prior to the end of the test period a bolus injection of 3 mg/kg, 1.5 mg/kg and 0.75 mg/kg of repaglinide is given. A RIST is taken and the result is greater insulin resistance than bethanechol or NAC alone. The lower doses of repaglinide are as effective as the higher dose.

Example 23

Hyperglycemic Control with Bethanechol and N-Acetylcysteine in Drug Naive Pre-Diabetic Males Objective—To determine the effectiveness of bethanechol and n-acetyl-cysteine (NAC) combination therapy in controlling postprandial hyperglycemia.

Summary of Study Design—The study is an open label study. The study subjects are pre/diabetic males 40-60 years, The trial involves at least 20 men and follows them through at least 12 weeks of treatment. Patients take the two compounds preferably one hour prior to their three major meals. The outcomes to be investigated are reductions in HbA1c levels either by >0.9% or below 7.5%, decrease in fasting glucose to <110 mg/dL, improving post prandial control of hyperglycemia/hyperinsulinemia, improvement of lipid profile (free fatty acids, TGs, and HDL/LDL cholesterol), reduction in blood pressure, weight loss and effect on liver function.

Inclusion Criteria—The subjects for the study are male subjects between the ages of 40 and 60, able to give informed consent, with mild to moderate type 2 diabetes (have HBA1c levels >8%, fasting glucose levels of >110 mb/dL), in otherwise good general health, with no other significant illnesses, blood pressure 160/90, with no known target organ damage.

End organ damage includes the following: proliferative retinopathy, serum creatinine greater than 2, ischemic heart disease, congestive heart failure, peripheral vascular disease and peripheral neuropathy.

Exclusion Criteria—Exclusion criteria include the following: significant digestive abnormalities such as malabsorption or chronic diarrhea; significant organ malfunction including (but not limited to) liver disease, pulmonary disease, ischemic heart disease, heart failure, stroke, peripheral vascular disease, hypertension (BP greater than 160/90), and anemia (hematocrit less than 30); other serious or chronic illness; history of serious or chronic illness; any significant complications from diabetes such as kidney damage (renal insufficiency, serum creatinine greater than 2), eye damage (proliferative retinopathy), diabetic neuropathy, coronary artery disease, or peripheral vascular disease; smoking, alcohol or drug abuse; insulin treatment; positive HIV or hepatitis (B or C) screening tests (subjects will be notified of these test results).

Patients on antihypertensive medication are excluded even if blood pressure is well controlled because antihypertensive medication may affect blood glucose during the test meal challenge, thus introducing a confounding variable.

Study Design—During the 12 week study the patient visits the clinic four times. At the first visit (prior to the start of the trial) the patient's baseline levels are measured by blood draw. The tests taken are: fasting glucose, TGs, AST, ALT, total bilirubin, alkaline phosphatase, HDL, LDL, total cholesterol, free fatty acids, fasting insulin, C-peptide and HbA1c. The patient then undergoes a Meal Tolerance Test using a standard can of Vanilla Boost as the model meal (237 ml with 10 g of protein, 4 g of fat and 41 carbohydrates). Blood samples are collected via an indwelling catheter and sent for analysis. The timeline is as follows:

| | |
|---|---|
| T = −1:10 (fasted) | glucose |
| T = −1:00 | glucose |
| | PATIENT WAITS ONE HOUR |
| T = 0:00 | glucose, Insulin, c-peptide, lactate, Free Fatty Acids (FFA), Glucagon, triglycerides (TGL) |
| | PATIENT CONSUMES BOOST LIQUID MEAL |
| T = 0:10 | glucose, Insulin, lactate, FFA |
| T = 0:20 | glucose, Insulin, lactate, FFA |
| T = 0:30 | glucose, Insulin, lactate, FFA |
| T = 0:45 | glucose, Insulin, lactate, FFA |
| T = 1:00 | glucose, Insulin, c-peptide, glucagon, lactate, FFA, TGL |
| T = 1:30 | glucose, Insulin, lactate, FFA |
| T = 2:00 | glucose, Insulin, c-peptide, glucagon, lactate, FFA, TGL |
| T = 3:00 | glucose, Insulin, c-peptide, glucagon, lactate, FFA, TGL |
| T = 4:00 | glucose, Insulin, c-peptide, glucagon, lactate, FFA, TGL |

The patients receives the drugs to take home. The drugs (bethanechol and N-acetylcysteine) are to be taken 1 hour prior to breakfast, lunch and dinner.

The second visit occurs 4 weeks after the start date. Physician checks patients blood pressure, weight and glucose. Patients fill out a simple questionnaire to determine if any other major changes in their lifestyle have occurred. Any left over drug is returned to the physician and counted and new drug is given to last the next four weeks.

Visit three occurs after 8 weeks. At the safety visit the physician again checks patients blood pressure, weight and glucose. Patients fill out a simple questionnaire to determine if any other major changes in their lifestyle have occurred. Old left over drug is returned to the physician and counted and new drug is released for the following four weeks.

During visit four which is at the 12 week mark the entire procedure of the first visit is repeated. Prior to the blood being withdrawn from the patient, he takes the combination therapy and then drinks the liquid test meal. The patient also the patient fills out the questionnaire.

Results—The combination therapy when taken prior to the meal positively affects at least one the endpoints.

REFERENCES

Beyer J, Krause U, Dobronz A, Fuchs B, Delver J R & Wagner R (1990). Assessment of Insulin Needs in Insulin-Dependent Diabetics and Healthy Volunteers Under Fasting Conditions. *Horm Metab Res Suppl* 24, 71-77.

Brownlee M (2001). Biochemistry and molecular cell biology of diabetic complications. Nature 414, 813-819.

Hsu C C, Yen H F, Yin M C, Tsai C M, Hsieh C H. Five cysteine-containing compounds delay diabetic deterioration in Balb/cA mice. J Nutr. 2004 December; 134 (12): 3245-9.

Latour M G & Chan C C (2002). A Rapid Insulin Sensitivity Test (RIST) in the Anesthetized Mice (Abstract). *Diabetes* 51 (Suppl. 2), A422.

Lautt W W (1999). The Hiss Story Overview: A Novel Hepatic Neurohumoral Regulation of Peripheral Insulin Sensitivity in Health and Diabetes. *Can J Physiol Pharmacol* 77, 553-562.

Lautt W W (2003). New Paradigm for Insulin Resistance: The Hiss Story. In: Atherosclerosis, Hypertension and Diabetes. Eds: G. N. Pierce, M. Nagano, P. Zahradka, And N. S. Dhalia. Kluwer Academic Publishers, Bost. Chapter 21, pp. 263-276.

Lautt W W, Macedo M P, Sadri P, Takayama S, Ramos F D & Legare D J (2001). Hepatic Parasympathetic Nerve-Dependent Control Of Peripheral Insulin Sensitivity Is Determined By Feeding And Fasting: Dynamic Control Of Hiss-Dependent Insulin Action. *Am J Physiol* 281, G29-G36.

Lautt, W. W., Wang, X., Sadri, P., Legare, D. J., And Macedo, M. P. (1998). Rapid Insulin Sensitivity Test (RIST). Can. J. Physiol. Pharmacol. 76: 1080-1086.

Ling P R, Mueller C, Smith R J, Bistrian B R. Hyperglycemia induced by glucose infusion causes hepatic oxidative stress and systemic inflammation, but not STAT3 or MAP kinase activation in liver in rats. Metabolism. 2003 July; 52 (7): 868-74.

Moore M C, Satake S, Baranowski B, Hsieh P S, Neal D W & Cherrington Ad (2002). Effect of Hepatic Denervation on Peripheral Insulin Sensitivity In Conscious Dogs. *Am J Physiol Endocrinol Metab* 282, E286-E296.

Porszasz R, Legvari G, Nemeth J, Literati P, Szolcsanyi J & Szilvassy Z (2002). The Sensory Nitrergic Nature of The Hepatic Insulin Sensitizing Substance Mechanism In Conscious Rabbits. *Eur. J Pharmacol* 443, 211-212.

Xie H & Lautt W W (1995). Induction of insulin resistance by cholinergic blockade with atropine in the cat. *J auton pharmacol* 15, 361-369.

The invention claimed is:

1. A pharmaceutical composition comprising: (a) bethanechol, (b) N-acetylcysteine, and (c) a pharmaceutically acceptable carrier, where the composition does not comprise a growth factor.

2. The pharmaceutical composition according to claim 1, wherein the bethanechol is nitrosylated.

3. The pharmaceutical composition according to claim 1, wherein the composition is a pharmaceutical salt thereof.

4. The pharmaceutical composition according to claim 1, further comprising a pharmaceutically acceptable liver targeting substance, wherein the liver targeting substance is selected from the group consisting of: albumin, a liposome, and a bile salt.

5. A method of treating or inhibiting type II diabetes, insulin resistance, or impaired glucose intolerance, comprising administering a therapeutically effective amount of the pharmaceutical composition according to claim 1.

6. The pharmaceutical composition according to claim 1, further comprising insulin or an insulin analogue.

7. The pharmaceutical composition according to claim 6, wherein the insulin analogue is lente insulin, semilente insulin, ultralente insulin, NPH or insulin lispro.

8. The pharmaceutical composition according to claim 1, further comprising an antioxidant.

9. The pharmaceutical composition according to claim 8, wherein the antioxidant is selected from the group consisting of: vitamin E, vitamin C, an isoflavone, zinc, selenium, ebselen, and a carotenoid.

10. The pharmaceutical composition according to claim 1, further comprising a glucagon like peptide (GLP) or glucagon like peptide analogue.

11. The pharmaceutical composition according to claim 10, wherein the glucagon like peptide analogue is selected from the group consisting of exanitide, DAC:GLP-1(CJC-1131), Liraglutide, ZP10, BIM51077, LY315902, and LY307161 (SR).

12. The pharmaceutical composition according to claim 1, further comprising alipoic acid.

13. The pharmaceutical composition according to claim 1, further comprising metformin.

14. The pharmaceutical composition according to claim 1, further comprising a sulphonylurea.

15. The pharmaceutical composition according to claim 14, wherein the sulphonylurea is selected is from the group consisting of: tolazamide, tolbutamide, chlorpropamide, acetohexamide, glyburide, glipizide, and glimepiride.

16. The pharmaceutical composition according to claim 1, further comprising carvedilol or labetolol.

17. The pharmaceutical composition according to claim 1, further comprising prazosin, doxazocin, phenoxybenzamine, terazosin, phentolamine, rauwolscine, yohimine, tolazoline, tamsulosin, carvedilol, or terazosin.

18. The pharmaceutical composition according to claim 1, further comprising acebutolol, atenolol, betaxolol, bisoprolol, carteolol, esmolol, metoprolol, nadolol, penbutolol, pindolol, propanolol, timolol, dobutamine hydrochloride, alprenolol, bunolol, bupranolol, carazolol, epanolol, moloprolol, oxprenolol, pamatolol, talinolol, tiprenolol, tolamolol, and toliprolol.

\* \* \* \* \*